United States Patent [19]

Sheridan

[11] Patent Number: 4,959,014
[45] Date of Patent: Sep. 25, 1990

[54] DENTAL SPACE MEASURING INSTRUMENT

[76] Inventor: John J. Sheridan, 1401 Lake St., Unit E-8, Metarie, La. 70005

[21] Appl. No.: 358,597

[22] Filed: May 30, 1989

[51] Int. Cl.⁵ .............................................. A61C 19/04
[52] U.S. Cl. ........................................ 433/72; 33/514
[58] Field of Search ................. 433/72, 2, 3; 33/513, 33/514, 531, 542, 662, 514.1

[56] References Cited

U.S. PATENT DOCUMENTS 4,473,952 10/1984 Mariani ................................. 33/542
4,624,639 11/1986 Wong ..................................... 433/72

Primary Examiner—Cary E. Stone
Attorney, Agent, or Firm—John M. Harrison

[57] ABSTRACT

A dental space measuring instrument for insertion in interdental or interproximal spaces between teeth in both the upper and lower dental arches to determine the width of such spaces for orthodontic treatment. The dental space measuring instrument is characterized by a centrally located handle provided with outwardly extending, graduated cylinders which define elongated, calibrated tips for insertion in the interdental spaces. The calibrated tips may be extended in a straight line from the handle or one or more cylinders in one or both of the calibrated tips may be angulated, and the diameter of each cylinder is indicated on the handle for size-identification purposes.

24 Claims, 1 Drawing Sheet

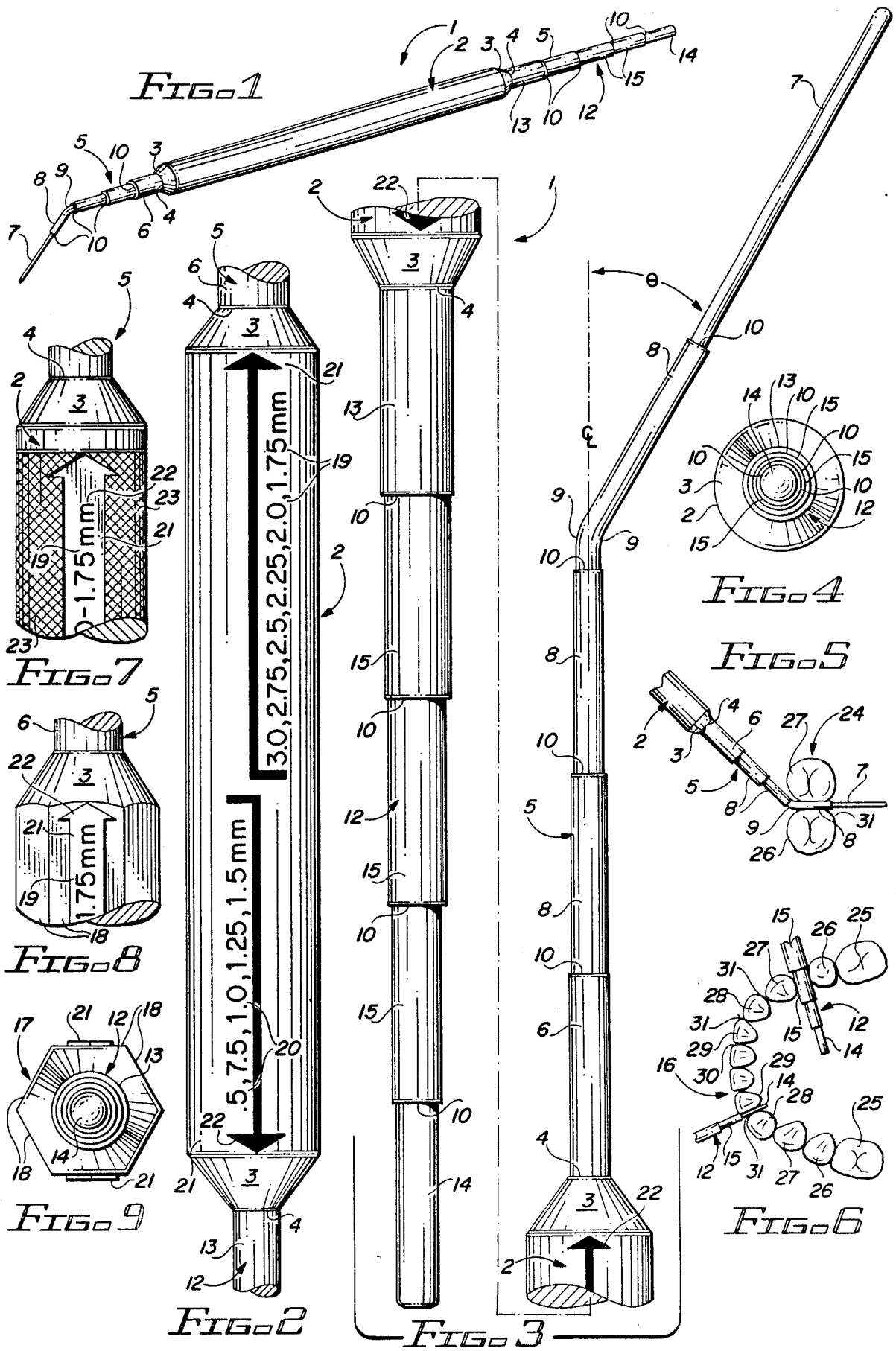

DENTAL SPACE MEASURING INSTRUMENT

BACKGROUND OF THE INVENTION

1. Field of the Invention

This invention relates to orthodontic instruments and more particularly, to a dental space measuring instrument which is designed for measuring naturally-occurring or mechanically-created interdental or interproximal spaces between teeth, to facilitate accurate orthodontic treatment of the teeth. In a preferred embodiment of the invention, the dental space measuring instrument is characterized by a handle having elongated calibrated tips extending from the ends thereof. The calibrated tips are characterized by multiple, graduated cylinders of selected diameter, length and number for accurate measurement of the interdental spaces. In a most preferred embodiment, at least one of the calibrated tips is angulated to facilitate convenient access to interdental spaces between the molars and bicuspids, between the bicuspids themselves, between the bicuspids and the adjacent cuspid teeth, and anterior incisor teeth. Numerical indicia which indicates the diameter of each discrete cylinder in the calibrated tips is provided on the handle and the handle may be round or shaped in the configuration of a polygon such as a hexagon, in non-exclusive particular.

One of the problems which exist in the practice of orthodontics is that of accurately measuring interdental or interproximal spaces, or the spaces between adjacent teeth in the dental arches, in order to correct spacing defects by well known orthodontic procedures. Accurate measurement of these interdental spaces is difficult, particularly when the spaces are located between the molars and the bicuspids, the bicuspids themselves or between the bicuspids and the cuspids, located at the back of, and centrally of the oral cavity, respectively. It is frequently necessary to determine this spacing, not only for restoration and cosmetic purposes, but also to prevent foodstuff from wedging between the teeth and causing discomfort, as well as potential periodontal disease.

2. Description of the Prior Art

Various types of devices are known in the field of orthodontics for measuring interdental spacing. Gauge plates having a variety of thicknesses have long been used for insertion in the interdental spaces, in order to measure the interproximal distance between adjacent teeth. These gauge plates are commonly known as dental contact gauges, usually constructed of stainless steel and are provided with a grip portion which may be color-coded according to the thickness of the plate. Since the average interproximal distance between teeth is on the order of about 70–92 microns in the case of young men and women, the three sizes of dental contact gauges which are normally used are 50 microns, 110 microns and 150 microns in thickness. In diagnosis, the gauge plates are inserted into the interdentium in order of plate thickness from the thinner gauge plate to the thicker one, until the succeeding gauge plate cannot be inserted therein. The dentist then estimates the interproximal distance under investigation according to data printed in a table provided with the instruments.

U.S. Pat. No. 4,664,627, dated May 12, 1987, to Ikuo Kyotani, details a "Dental Contact Gauge" which is used for the examination of proximal spacing between adjacent teeth. The gauge is characterized by a gauge plate having a constant thickness and formed of a shape-memory alloy to facilitate conforming the gauge approximately to the contour of the adjacent teeth. The gauge is subsequently restored to its original shape at a temperature of at least 40 degrees Centigrade.

Tools used to probe the depth of cavities and for other purposes in the practice of dentistry are also well known in the art. An early dental tool is detailed in U.S. Pat. No. 1,501,170, dated July 15, 1924, to F. W. Korb. The Korb measuring tool includes an elongated sleeve, one end of which is provided with an annular, radial rib shaped in the form of a collar and carried by a shell or guard member which is securely arranged over the sleeve end. The shell or guard extends over the sleeve a distance sufficient to entirely cover slits provided in the sleeve, in order to prevent accidental injury to the operator by a probe which is extended through one of the slits. The shell is provided with a pair of oppositely-disposed apertures, through which an instrument may be inserted to increase the tension in the gripping jaw. The rib or collar serves as a finger-piece for the user while adjusting the instrument. The forward end of the sleeve is snugly fitted within the inner end of a nipple which is tapered and curved to a comparatively small end adapted to rest upon a tooth at the entrance of a cavity, the depth of which is to be measured. In use, the end of the probe is inserted to the bottom of the cavity in the tooth and the operator then moves the sleeve forwardly until the tapered end contacts the tooth at the entrance to the cavity. The tool is then removed from the patient's mouth and the projecting portion of the probe is measured by a scale or rule to accurately determine the depth of the cavity in the tooth. A "Remote-Recording Periodontal Depth Probe" is detailed in U.S. Pat. No. 3,943,914, dated Mar. 16, 1976. The apparatus includes a protruding, removably attached, cylindrical probe tip which is partially ensheathed by a slidable tubular sleeve that is electrically connected by means of a transducer within the probe body to a remote recording device. Translational movement of the slidable tubular sleeve which partially sheaths the probe tip varies an electrical signal between the probe and the remote recording device according to the length of probe tip exposed. An operator-controlled foot switch is connected between the probe and the remote recording device, which arrangement allows the operator to insert the probe tip into the gingival sulcus and to adjust the slidable sleeve until it touches the margin of the gingiva before activating the remote recording device. When activated, the recorder produces a record of the electrical signal which corresponds to the length of the exposed probe tip and this record is representative of the depth of the gingival sulcus at the measured location. A periodontal probe is detailed in U.S. Pat. No. 4,364,730, dated Dec. 21, 1982, to Per A. T. Axelsson. The probe is characterized by a handle portion and a pin member rotatably mounted on the handle portion about an axis of rotation. The pin member further includes a free end portion which is straight and flat and lies to one side of and in the same plane as the axis of rotation. The spacing between the free end portion and the axis is either constant or decreases in a direction toward the free end of the free end portion. U.S. Pat. No. 4,677,756, dated July 7, 1987, to Louis A. Simon, et al, details "Measuring Instruments for Measuring the Depth of Cavities". In a preferred embodiment a probe device includes a probe element and a sheath, the probe element being slidable within the sheath and protruding therefrom in variable length. Further included is a means for producing a depth signal representing the amount of protrusion of the probe element from the sheath, means for monitoring the rate of change of the depth signal and means for recording and/or displaying a value which is representative of the depth signal when the rate of change of the depth signal reaches a predetermined value.

It is an object of this invention to provide a new and improved dental space measuring instrument for measuring interdental spaces in the upper and lower dental arches.

Another object of the invention is to provide a dental space measuring instrument which is characterized by a quantifiable gauge adapted to measure interdental spaces which are either mechanically created or naturally occurring.

Still another object of this invention is to provide a dental space measuring instrument which is characterized by a centrally located handle and at least one set of graduated cylinders extending from the handle for insertion between adjacent teeth in the dental arch to determine the size of the interdental spaces with a high degree of accuracy.

Still another object of the invention is to provide a dental space measuring instrument which includes a handle and at least one elongated, calibrated tip defined by a set of graduated cylinders extending from the handle, which graduated cylinders may either be straight or angulated for insertion in spaces between the teeth to determine the width of such spaces and facilitate accurate orthodontic treatment.

Yet another object of the invention is to provide a dental space measuring instrument which is characterized by a handle, a first elongated, calibrated tip of selected length characterized by a first set of graduated cylinders extending from one end of the handle in a straight line, and a second elongated, calibrated tip of selected length defined by a second set of graduated cylinders extending from the opposite end of the handle in angulated relationship, wherein the graduated cylinders may be inserted in interdental spaces in the upper and lower dental arches to determine the magnitude of the interdental spaces, for orthodontic treatment.

SUMMARY OF THE INVENTION

These and other objects of the invention are provided in a new and improved dental space measuring instrument which is characterized by an elongated handle having a first calibrated tip defined by a first set of graduated cylinders extending from one end thereof in a straight line, a second calibrated tip defined by a second set of graduated cylinders extending from the opposite end of the handle, which second calibrated set of graduated cylinders are angulated at a selected point, and appropriate indicia provided on the handle for identifying the diameter of each graduated cylinder, such that the cylinders can be inserted in interdental spaces in the upper and lower dental arches to determine the width of the interdental spaces and facilitate accurate orthodontic treatment.

BRIEF DESCRIPTION OF THE DRAWING

The invention will be better understood by reference to the accompanying drawing, wherein:

FIG. 1 is a perspective view of a preferred embodiment of the dental space measuring instrument of this invention;

FIG. 2 is an enlarged view, partially in section, of the handle portion of the dental space measuring instrument illustrated in FIG. 1;

FIG. 3 is an enlarged view, partially in section, of the calibrated angulated tip and calibrated straight tip elements of the dental space measuring instrument illustrated in FIG. 1;

FIG. 4 is an end view of the calibrated straight tip element of the dental space measuring instrument illustrated in FIGS. 1 and 3;

FIG. 5 is a perspective view, partially in section, of the dental space measuring instrument illustrated in FIG. 1, with the calibrated angulated tip inserted in a typical interdental space;

FIG. 6 is a perspective view, partially in section, of the dental space measuring instrument illustrated in FIG. 1, with a pair of calibrated straight tips inserted into separate interdental spaces of varying width in a lower dental arch;

FIG. 7 is a side view, partially in section, of an alternative handle configuration for the dental space measuring instrument illustrated in FIG. 1;

FIG. 8 is a side view, partially in section, of yet another alternative handle embodiment of the dental space measuring instrument illustrated in FIG. 1; and FIG. 9 is an end view of the handle embodiment of the calibrated straight tip element of the dental space measuring instrument illustrated in FIG. 8.

DESCRIPTION OF THE PREFERRED EMBODIMENTS

Referring initially to FIGS. 1-4 of the drawing, the dental space measuring instrument of this invention is generally indicated by reference numeral 1. The dental space measuring instrument 1 includes a round handle 2 provided with a handle taper 3 at each end, which handle taper 3 terminates at a taper margin 4. A calibrated angulated tip 5 projects from the round handle 2 and is defined by a proximal angulated cylinder 6, which extends from the round handle 2 at the taper margin 4, three graduated intermediate cylinders 8, projecting from the proximal angulated cylinder 6 in end-to-end relationship and a distal angulated cylinder 7, which extends from the first intermediate cylinder 8 and terminates the extending end of the calibrated angulated tip 5. The proximal angulated cylinder 6, intermediate angulated cylinders 8 and distal angulated cylinder 7 are graduated in decreasing diameter at each of the cylinder shoulders 10, which define cylinder junctions. A cylinder bend 9 is provided in the first extending intermediate angulated cylinder 8, in order to facilitate reaching interdental spaces which are located centrally and in the rear of the oral cavity, as hereinafter further described.

A calibrated straight tip 12 projects from the opposite end of the round handle 2 and is defined by a proximal straight cylinder 13, extending from the round handle 2 at the taper margin 4 of the handle taper 3, three intermediate straight cylinders 15 extending from the proximal straight cylinder 13 in end-to-end relationship and a distal straight cylinder 14 terminating the extending end of the straight tip 12 and projecting from the first intermediate straight cylinder 15. As in the case of the calibrated angulated tip 5, the proximal straight cylinder 13, intermediate straight cylinders 15 and distal straight cylinder 14 which define the calibrated straight tip 12, are graduated in decreasing diameter at the spaced cylinder shoulders 10. As further illustrated in FIG. 2, angulated cylinder indicia 19 and straight cylinder indicia 20 are provided on an indicia base 21 located on the handle 2 and an indicia arrow 22 indicates that the angulated cylinder indicia 19 is appropriate for designating the relative sizes of the proximal angulated cylinder 6, intermediate angulated cylinders 8 and the distal angulated cylinder 7, respectively, which define the calibrated angulated tip 5. Similarly, the straight cylinder indicia 20 and the opposite indicia arrow 22 identify the relative diameter of the proximal straight cylinder 13, intermediate straight cylinders 15 and distal straight cylinder 14, respectively, which comprise the calibrated straight tip 12.

Referring now to FIGS. 8 and 9, in another preferred embodiment of the invention the dental space measuring instrument 1 is characterized by a hexagonal handle 17, having six flat handle facets 18. Otherwise, the calibrated angulated tip 5 and the calibrated straight tip 12 of the dental space measuring instrument 1 is identical to the configuration illustrated in FIGS. 1–4.

As further illustrated in FIG. 7, a knurled surface 23 may be provided in the round handle 2 and the indicia base 21 may be elevated from or coextensive with the knurled surface 23, in order to facilitate stamping or otherwise providing the angulated cylinder indicia 19 and the straight cylinder indicia 20 thereon in a selected order.

Referring to FIGS. 2 and 5 of the drawing, a pair of teeth 24 characterized by a second premolar 26 and an adjacent first premolar 27 is illustrated, with the first intermediate angulated cylinder 8 of the calibrated angulated tip 5 extending to the interproximal space therebetween, for measurement purposes. Since the second premolar 26 and the first premolar 27 are located near the rear of the oral cavity, the cylinder bend 9 serves to facilitate easy manipulation of the distal angulated cylinder 7 and the adjacent first intermediate angulated cylinder 8 into the interdental space 31 to accurately determine the width of the interdental space 31. In this case, the interdental spacing is equal to the diameter of the first intermediate angulated cylinder 8, which diameter is determined by viewing the angulated cylinder indicia 19 in order of cylinder appearance from the end of the angulated tip 5, reading from the indicia arrow 22. Accordingly, the interproximal space between the second premolar 26 and the first premolar 27 is 2 millimeters, as noted in the angulated cylinder indicia 19 in FIG. 2.

Referring now to FIG. 6 of the drawing, a pair of calibrated straight tips 12 of the dental space measuring instrument 1 illustrated in FIGS. 1–4 are inserted in the interdental spaces 31 located between the second premolar 26 and the first premolar 27, as well as between the cuspid 28 and the lateral incisor 29, respectively, in the lower dental arch 16, which is anchored by the molars 25. In the first case, the straight end 12 is projected into the interdental space 31 such that the distal straight cylinder 14 and the first intermediate straight cylinder 15 enter the oral cavity 30, while the second intermediate straight cylinder 15 fits with a close tolerance between the second premolar 26 and the first premolar 27. Accordingly, the straight cylinder indicia 20, located on the indicia base 21 of the round handle 2 illustrated in FIG. 2, is reviewed and measuring from the indicia arrow 22, the straight cylinder indicia 20 indicates that the diameter of the second intermediate straight cylinder 15 is 1 millimeter. The interdental space 31 between the second premolar 26 and the first premolar 27 is therefore 1 millimeter in width and these teeth can be orthodontically treated accordingly. Under circumstances where the straight end 12 of the dental space measuring instrument 1 is inserted between the cuspid 28 and the lateral incisor 29, the interdental space 31 is large enough to receive the distal straight cylinder 14, but not sufficiently large to allow insertion of the first intermediate straight cylinder 15. Accordingly, it is concluded that the interdental space 31 between the cuspid 28 and the lateral incisor 29 is one-half of a millimeter in width, as noted in the straight cylinder indicia 20 located on the round handle 2.

It will be appreciated by those skilled in the art that the dental space measuring instrument of this invention offers a highly versatile, easily manipulated and efficient tool for measuring the interdental spaces 31 located in both the upper and lower dental arches. It is understood that while the dental space measuring instrument illustrated in the drawing is characterized by a calibrated angulated tip 5 and a calibrated straight tip 12, each having 5 graduated cylinders, the number of graduated cylinders, as well as the location of the cylinder bend 9 in the calibrated angulated tip 5, is a matter of discretion according to the desire of the user. For example, the cylinder bend 9 may be located closer to the taper margin 4 or to the distal angulated cylinder 7, as desired, in order to better reach the molar 25, the second premolar 26 and first premolar 27. Furthermore, the size and number of cylinders in both the calibrated angulated end 5 and the calibrated straight end 12 can be selected according to variation in the size, location and frequency of interdental spaces 31 in children and adults, respectively. Moreover, while the length of the proximal angulated cylinder 6, distal angulated cylinder 7, intermediate angulated cylinders 8, proximal straight cylinder 13, distal straight cylinder 14 and intermediate straight cylinders 15 may be varied, in a most preferred embodiment, this length is about 5 mm. Typical, but non-exclusive diameter measurements are 1.75, 2.0, 2.25, 2.5 and 2.75 millimeters for the distal angulated cylinder 7, intermediate angulated cylinders 8 and proximal angulated cylinder 6, respectively, and 0.5, 0.75, 1.0, 1.25, and 1.5 mm. for the distal straight cylinder 14, intermediate straight cylinders 15 and proximal straight cylinder 13, respectively, as indicated in the angulated cylinder indicia 19 and the straight cylinder indicia 20, respectively, provided on the indicia base 21 of the round handle 2, illustrated in FIG. 2. However, it will be appreciated that other diameter measurements which are indicated in any desired units may also be used, as desired. As heretofore described, the cross-sectional configuration of the round handle 2 can be altered to define the hexagonal handle 17 or a handle shaped in the configuration of any regular polygon, or in any other configuration, as desired. Moreover, it will be further recognized that while stainless steel is the preferred material of choice for the dental space measuring instrument 1 since it can be sterilized in an autoclave, other materials of construction can be utilized, including injection-molded plastics, fiberglass and like resilient materials, and even wood, wherein the dental space measuring instrument 1 is discarded after each use.

While the preferred embodiments of the invention have been described above, it will be recognized and understood that various modifications may be made therein and the appended claims are intended to cover all such modifications which may fall within the spirit and scope of the invention.

Having described my invention with the particularity set forth above, what is claimed is:

1. A dental space measuring instrument for measuring the spacing between teeth, comprising handle means and at least one first straight portion extending from said handle means and an angulated portion extending from said first straight portion in angular relationship, said first straight portion and said angulated portion further defined by a first plurality of graduated measuring means adapted for insertion between the teeth and measuring the spacing.

2. The dental measuring instrument of claim 1 further comprising a second straight portion extending from said handle means, said second straight portion defined by a second plurality of graduated measuring means.

3. The dental space measuring instrument of claim 2 wherein said second plurality of graduated measuring means further comprises a second plurality of graduated cylinders, with the largest of said second plurality of graduated cylinders extending from one end of said handle means.

4. The dental space measuring instrument of claim 2 wherein:
   (a) said first plurality of said graduated measuring means further comprises a first plurality of graduated cylinders, with the largest of said first plurality of graduated cylinders extending from one end of said handle means; and
   (b) said second plurality of said graduated measuring means further comprises a second plurality of graduated cylinders, with the largest of said second plurality of graduated cylinders extending from the opposite end of said handle means.

5. The dental space measuring instrument of claim 2 further comprising an angulated portion extending from said second straight portion in angular relationship, respectively, said second straight portion and said angulated portion further defined by a second plurality of said graduated measuring means.

6. The dental space measuring instrument of claim 5 wherein said plurality of said graduated measuring means further comprises a plurality of graduated cylinders, with the largest of said graduated cylinders extending from said one end and said opposite end of said handle means, respectively.

7. The dental space measuring instrument of claim 2 further comprising measuring indicia provided on said handle means for indicating the size of said graduated measuring means, respectively.

8. The dental space measuring instrument of claim 7 wherein:
   (a) said first plurality of said graduated measuring means further comprises a first plurality of graduated cylinders, with the largest of said first plurality of graduated cylinders extending from one end of said handle means;
   (b) said second plurality of said graduated measuring means further comprises a second plurality of graduated cylinders, with the largest of said second plurality of graduated cylinders extending from the opposite end of said handle means; and
   (c) said measuring indicia corresponds to the diameter of said first plurality of graduated cylinders and said second plurality of graduated cylinders, respectively.

9. The dental space measuring instrument of claim 1 wherein said first plurality of graduated measuring means further comprises a first plurality of graduated cylinders, with the largest of said first plurality of graduated cylinders extending from said one end of said handle means.

10. An instrument for measuring the interproximal space between teeth, comprising a handle, a first plurality of graduated cylinders projecting from one end of said handle and a second plurality of graduated cylinders projecting from the opposite end of said handle, whereby said first plurality of graduated cylinders and said second plurality of graduated cylinders are selectively inserted in the interproximal space for measuring the width of the interproximal space.

11. The instrument of claim 10 wherein selected ones of said first plurality of graduated cylinders are angulated with respect to the longitudinal plane of said handle.

12. The instrument of claim 10 wherein said second plurality of graduated cylinders project from said opposite end of said handle substantially in the longitudinal plane of said handle.

13. The instrument of claim 10 wherein selected ones of said first plurality of graduated cylinders are angulated with respect to the longitudinal plane of said handle and said second plurality of graduated cylinders project from said opposite end of said handle substantially in the longitudinal plane of said handle.

14. The instrument of claim 10 further comprising first numerical indicia provided on said handle for indicating the diameter of said first plurality of graduated cylinders and second numerical indicia provided on said handle for indicating the diameter of said second plurality of graduated cylinders.

15. The instrument of claim 14 wherein selected ones of said first plurality of graduated cylinders are angulated with respect to the longitudinal plane of said handle and said second plurality of graduated cylinders project from said opposite end of said handle substantially in the longitudinal plane of said handle.

16. An instrument for measuring interdental spaces, comprising an elongated handle, a first plurality of graduated cylinders projecting from one end of said handle, with the largest one of said first plurality of graduated cylinders extending from said one end of said handle and a second plurality of graduated cylinders projecting from the opposite end of said handle, with the largest one of said second plurality of graduated cylinders extending from said opposite end of said handle, whereby said first plurality of graduated cylinders and said second plurality of graduated cylinders are selectively inserted in the interdental spaces for measuring the width of the interdental spaces.

17. The instrument of claim 16 wherein selected ones of said first plurality of graduated cylinders are angulated with respect to the longitudinal plane of said handle.

18. The instrument of claim 16 wherein said second plurality of graduated cylinders project from said opposite end of said handle substantially in the longitudinal plane of said handle.

19. The instrument of claim 16 wherein selected ones of said first plurality of graduated cylinders are angulated with respect to the longitudinal plane of said handle and said second plurality of graduated cylinders project from said opposite end of said handle substantially in the longitudinal plane of said handle.

20. The instrument of claim 16 further comprising first numerical indicia provided on said handle for indicating the diameter of said first plurality of graduated cylinders and second numerical indicia provided on said handle for indicating the diameter of said second plurality of graduated cylinders.

21. The instrument of claim 20 wherein selected ones of said first plurality of graduated cylinders are angulated with respect to the longitudinal plane of said handle.

22. The instrument of claim 20 wherein second plurality of graduated cylinders project from said opposite end of said handle substantially in the longitudinal plane of said handle.

23. The instrument of claim 20 wherein selected ones of said first plurality of graduated cylinders are angulated with respect to the longitudinal plane of said handle and said second plurality of graduated cylinders project from said opposite end of said handle substantially in the longitudinal plane of said handle.

24. The instrument of claim 23 further comprising arrow indicia provided on said handle for indicating which of said numerical indicia is applicable to said first plurality of graduated cylinders and said second plurality of graduated cylinders, respectively.

* * * * *